(12) United States Patent
Olien et al.

(10) Patent No.: US 7,877,243 B2
(45) Date of Patent: Jan. 25, 2011

(54) PIVOTABLE COMPUTER INTERFACE

(75) Inventors: Neil T. Olien, San Jose, CA (US); Pedro Gregorio, San Jose, CA (US); David W. Bailey, San Jose, CA (US); Steven P. Vassallo, San Jose, CA (US)

(73) Assignee: Immersion Corporation, San Jose, CA (US)

( * ) Notice: Subject to any disclaimer, the term of this patent is extended or adjusted under 35 U.S.C. 154(b) by 1911 days.

(21) Appl. No.: 10/196,717

(22) Filed: Jul. 15, 2002

(65) Prior Publication Data

US 2003/0025723 A1 Feb. 6, 2003

Related U.S. Application Data

(60) Provisional application No. 60/305,958, filed on Jul. 16, 2001.

(51) Int. Cl.
*G06G 7/48* (2006.01)
*G09G 5/00* (2006.01)
*G09G 5/08* (2006.01)

(52) U.S. Cl. .............................. 703/3; 345/156; 345/161
(58) Field of Classification Search ................... 703/13, 703/6; 345/161, 156
See application file for complete search history.

(56) References Cited

U.S. PATENT DOCUMENTS

| | | |
|---|---|---|
| 3,157,853 A | 11/1964 | Hirsch |
| 3,220,121 A | 11/1965 | Cutler |
| 3,497,668 A | 2/1970 | Hirsch |
| 3,517,446 A | 6/1970 | Corlyon et al. |
| 3,902,687 A | 9/1975 | Hightower |
| 3,903,614 A | 9/1975 | Diamond et al. |
| 4,160,508 A | 7/1979 | Salisbury, Jr. et al. |
| 4,236,325 A | 12/1980 | Hall et al. |
| 4,513,235 A | 4/1985 | Acklam et al. |
| 4,581,491 A | 4/1986 | Boothroyd |
| 4,581,972 A | 4/1986 | Hoshino |
| 4,599,070 A | 7/1986 | Hladky et al. |
| 4,708,656 A | 11/1987 | De Vries et al. |
| 4,713,007 A | 12/1987 | Alban |

(Continued)

FOREIGN PATENT DOCUMENTS

EP 0349086 1/1990

(Continued)

OTHER PUBLICATIONS

Shimoga, K., A Survey of Perceptual Feedback Issues in Dexterous Telemanipulation: Part I. Finger Force Feedback, IEEE Annual International Symposium on Virtual Reality, Sep. 18, 1993, pp. 263-270.

(Continued)

*Primary Examiner*—Paul L Rodriguez
*Assistant Examiner*—Andre Pierre Louis
(74) *Attorney, Agent, or Firm*—Kilpatrick Stockton LLP

(57) ABSTRACT

A computer interface for use with a computer simulation system. The interface includes a first grip portion and a second grip portion pivotably coupled to the first grip portion. An actuator is coupled to at least one of the two grip portions and is configured to provide feedback to a user.

20 Claims, 12 Drawing Sheets

U.S. PATENT DOCUMENTS

| | | | |
|---|---|---|---|
| 4,731,603 A | 3/1988 | McRae et al. | |
| 4,795,296 A | 1/1989 | Jau | |
| 4,831,531 A | 5/1989 | Adams et al. | |
| 4,861,269 A | 8/1989 | Meenen, Jr. | |
| 4,891,764 A | 1/1990 | McIntosh | |
| 4,907,970 A | 3/1990 | Meenen, Jr. | |
| 4,930,770 A | 6/1990 | Baker | |
| 4,934,694 A | 6/1990 | McIntosh | |
| 4,935,728 A | 6/1990 | Kley | |
| 4,986,280 A | 1/1991 | Marcus et al. | |
| 5,019,761 A | 5/1991 | Kraft | |
| 5,022,407 A | 6/1991 | Horch et al. | |
| 5,035,242 A | 7/1991 | Franklin | |
| 5,038,089 A | 8/1991 | Szakaly | |
| 5,078,152 A | 1/1992 | Bond | |
| 5,116,180 A | 5/1992 | Fung et al. | |
| 5,142,931 A | 9/1992 | Menahem | |
| 5,143,505 A | 9/1992 | Burdea et al. | |
| 5,156,363 A | 10/1992 | Cizewski et al. | |
| 5,182,557 A | 1/1993 | Lang | |
| 5,186,695 A | 2/1993 | Mangseth et al. | |
| 5,212,473 A | 5/1993 | Louis | |
| 5,240,417 A | 8/1993 | Smithson et al. | |
| 5,251,127 A | 10/1993 | Raab | |
| 5,271,290 A | 12/1993 | Fischer | |
| 5,275,174 A | 1/1994 | Cook | |
| 5,289,273 A | 2/1994 | Lang | |
| 5,299,810 A | 4/1994 | Pierce | |
| 5,309,140 A | 5/1994 | Everett | |
| 5,334,027 A | 8/1994 | Wherlock | |
| 5,397,323 A | 3/1995 | Taylor et al. | |
| 5,402,499 A | 3/1995 | Robison et al. | |
| 5,435,554 A | 7/1995 | Lipson | |
| 5,436,542 A | 7/1995 | Petelin et al. | |
| 5,438,529 A | 8/1995 | Rosenberg et al. | |
| 5,451,924 A | 9/1995 | Massimino et al. | |
| 5,452,615 A | 9/1995 | Hilton | |
| 5,466,213 A | 11/1995 | Hogan | |
| 5,491,477 A | 2/1996 | Clark et al. | |
| 5,547,382 A | 8/1996 | Yamasaki | |
| 5,562,707 A | 10/1996 | Prochazka | |
| 5,565,840 A | 10/1996 | Thorner et al. | |
| 5,583,407 A | 12/1996 | Yamaguchi | |
| 5,609,485 A | 3/1997 | Bergman et al. | |
| 5,623,582 A | 4/1997 | Rosenberg | |
| 5,669,818 A | 9/1997 | Thorner et al. | |
| 5,684,722 A | 11/1997 | Thorner et al. | |
| 5,715,412 A | 2/1998 | Aritsuka et al. | |
| 5,731,804 A * | 3/1998 | Rosenberg | 345/156 |
| 5,736,978 A | 4/1998 | Hasser et al. | |
| 5,745,057 A | 4/1998 | Sasaki et al. | |
| 5,766,016 A | 6/1998 | Sinclair | |
| 5,767,457 A | 6/1998 | Gerpheide et al. | |
| 5,769,640 A | 6/1998 | Jacobus et al. | |
| 5,785,630 A | 7/1998 | Bobick et al. | |
| 5,800,177 A | 9/1998 | Gillio | |
| 5,808,665 A | 9/1998 | Green | |
| 5,816,105 A | 10/1998 | Adelstein | |
| 5,844,392 A | 12/1998 | Peurach et al. | |
| 5,857,986 A | 1/1999 | Moriyasu | |
| 5,894,263 A | 4/1999 | Shimakawa et al. | |
| 6,005,551 A | 12/1999 | Osborne et al. | |
| 6,037,927 A | 3/2000 | Rosenberg | |
| 6,111,577 A | 8/2000 | Zilles et al. | |
| 6,131,097 A | 10/2000 | Peurach et al. | |
| 6,184,868 B1 * | 2/2001 | Shahoian et al. | 345/161 |
| 6,201,524 B1 | 3/2001 | Aizawa | |
| 6,219,034 B1 | 4/2001 | Elbing et al. | |
| 6,246,390 B1 | 6/2001 | Rosenberg | |
| 6,285,351 B1 | 9/2001 | Chang et al. | |
| 6,292,170 B1 | 9/2001 | Chang et al. | |
| 6,300,936 B1 | 10/2001 | Braun et al. | |
| 6,323,837 B1 | 11/2001 | Rosenberg | |
| 6,374,255 B1 | 4/2002 | Peurach et al. | |
| 6,380,925 B1 * | 4/2002 | Martin et al. | 345/161 |
| 6,422,941 B1 | 7/2002 | Thorner et al. | |
| 6,424,356 B2 | 7/2002 | Chang et al. | |
| 6,433,771 B1 | 8/2002 | Yocum et al. | |
| 6,697,044 B2 * | 2/2004 | Shahoian et al. | 345/156 |
| 6,906,697 B2 * | 6/2005 | Rosenberg | 345/156 |
| 2001/0016804 A1 | 8/2001 | Cunningham et al. | |
| 2003/0067440 A1 | 4/2003 | Rank | |
| 2003/0068053 A1 | 4/2003 | Chu | |
| 2004/0056840 A1 * | 3/2004 | Goldenberg et al. | 345/156 |
| 2005/0162383 A1 * | 7/2005 | Rosenberg | 345/156 |

FOREIGN PATENT DOCUMENTS

| | | |
|---|---|---|
| GB | 2 307 030 | 5/1997 |
| JP | 01-003664 | 7/1990 |
| JP | 02-109714 | 1/1992 |
| JP | 04-007371 | 8/1993 |
| JP | 05-193862 | 1/1995 |
| JP | 09-019879 | 1/1997 |
| JP | 2000-148382 | 5/2000 |
| JP | 2000-181618 | 6/2000 |
| JP | 2000-357048 | 12/2000 |
| WO | WO 9216141 | 10/1992 |
| WO | WO 9426167 | 11/1994 |
| WO | WO 9502233 | 1/1995 |
| WO | WO 9639944 | 12/1996 |
| WO | WO 01/41052 | 6/2001 |

OTHER PUBLICATIONS

European Patent Office, Supplementary European Search Report, Application No. 02748179.5, mailed Apr. 20, 2009.

Patent Office of the Peoples Republic of China, First Office Action, Application No. 02814354.X, issued Oct. 14, 2005.

Japanese Patent Office, Notice of Final Rejection, Application No. 2003-514482, mailed Sep. 25, 2007.

Japanese Patent Office, Notice of Reasons for Rejection, Application No. 2003-514482, mailed Jun. 12, 2007.

Korean Patent Office, Notice of Preliminary Rejection, Application No. 10-2004-7000604, mailed Jun. 17, 2008.

Korean Patent Office, Notice of Final Rejection, Application No. 10-2004-7000604, mailed Jan. 6, 2009.

European Patent Office, Communication Pursuant to Article 94(3) EPC, Application No. 02748179.5, mailed Dec. 12, 2009.

Adelstein, "A Virtual Environment System for the Study of Human Arm Tremor," Ph.D. Dissertation, Dept of Mechanical Engineering, MIT, Jun. 1989.

Adelstein, "Design and Implementation of a Force Reflecting Manipulandum for Manual Control research," DSC- vol. 42, Advances in Robotics, Edited by H. Kazerooni, pp. 1-12, 1992.

Aukstakalnis et al., "Silicon Mirage: The Art and Science of Virtual Reality," ISBN 0-938151-82-7, pp. 129-180, 1992.

Baigrie, "Electric Control Loading—A Low Cost, High Performance Alternative," Proceedings, pp. 247-254, Nov. 6-8, 1990.

Bejczy et al., "Kinesthetic Coupling Between Operator and Remote Manipulator," International Computer Technology Conference, The American Society of Mechanical Engineers, San Francisco, CA, Aug. 12-15, 1980.

Bejczy, "Sensors, Controls, and Man-Machine Interface for Advanced Teleoperation," Science, vol. 208. No. 4450, pp. 1327-1335, 1980.

Bejczy, "Generalization of Bilateral Force-Reflecting Control of Manipulators," Proceedings of Fourth CISM-IFToMM, Sep. 8-12, 1981.

Bejczy, et al., "Universal Computer Control System (UCCS) For Space Telerobots," CH2413-3/87/0000/0318501.00 1987 IEEE, 1987.

Bejczy et al., "A Laboratory Breadboard System for Dual-Arm Teleoperation," SOAR '89 Workshop, JSC, Houston, TX, Jul. 25-27, 1989.

Brooks et al., "Hand Controllers for Teleoperation—A State-of-the-Art Technology Survey and Evaluation," JPL Publication 85-11; NASA-CR-175890; N85-28559, pp. 1-84, Mar. 1, 1985.

Burdea et al., "Distributed Virtual Force Feedback, Lecture Notes for Workshop on Force Display in Virtual Environments and its Application to Robotic Teleoperation," 1993 IEEE International Conference on Robotics and Automation, pp. 25-44, May 2, 1993.

Caldwell et al., "Enhanced Tactile Feedback (Tele-Taction) Using a Multi-Functional Sensory System," 1050-4729/93, pp. 955-960, 1993.

"Cyberman Technical Specification," Logitech Cyberman SWIFT Supplement, Apr. 5, 1994.

Eberhardt et al., "OMAR—A Haptic display for speech perception by deaf and deaf-blind individuals," IEEE Virtual Reality Annual International Symposium, Seattle, WA, Sep. 18-22, 1993.

Eberhardt et al., "Including Dynamic Haptic Perception by The Hand: System Description and Some Results," DSC-vol. 55-1, Dynamic Systems and Control: vol. 1, ASME 1994.

Gobel et al., "Tactile Feedback Applied to Computer Mice," International Journal of Human-Computer Interaction, vol. 7, No. 1, pp. 1-24, 1995.

Gotow et al., "Controlled Impedance Test Apparatus for Studying Human Interpretation of Kinesthetic Feedback," WA11-11:00, pp. 332-337, 1989.

Howe, "A Force-Reflecting Teleoperated Hand System for the Study of Tactile Sensing in Precision Manipulation," Proceedings of the 1992 IEEE International Conference on Robotics and Automation, Nice, France, May 1992.

IBM Technical Disclosure Bullein, "Mouse Ball-Actuating Device With Force and Tactile Feedback," vol. 32, No. 9B, Feb. 1990.

Iwata, "Pen-based Haptic Virtual Environment," 0-7803-1363-1/93 IEEE, pp. 287-292, 1993.

Jacobsen et al., "High Performance, Dextrous Telerobotic Manipulator With Force Reflection," Intervention/ROV '91 Conference & Exposition, Hollywood, Florida, May 21-23, 1991.

Jones et al., "A perceptual analysis of stiffness," ISSN 0014-4819 Springer International (Springer-Verlag); Experimental Brain Research, vol. 79, No. 1, pp. 150-156, 1990.

Kaczmarek et al., "Tactile Displays," Virtual Environment Technologies, 1995.

Kontarinis et al., "Display of High-Frequency Tactile Information to Teleoperators," Telemaniputator Technology and Space Telerobotics, Won S. Kim, Editor, Proc. SPIE vol. 2057, pp. 40-50, Sep. 7-9, 1993.

Marcus, "Touch Feedback in Surgery," Proceedings of Virtual Reality and Medicine The Cutting Edge, Sep. 8-11, 1994.

McAffee, "Teleoperator Subsystem/Telerobot Demonsdtrator: Force Reflecting Hand Controller Equipment Manual," JPL D-5172, pp. 1-50, A1-A36, B1-B5, C1-C36, Jan. 1988.

Minsky, "Computational Haptics: The Sandpaper System for Synthesizing Texture for a Force-Feedback Display," Ph.D. Dissertation, MIT, Jun. 1995.

Ouh-Young, "Force Display in Molecular Docking," Order No. 9034744, p. 1-369, 1990.

Ouh-Young, "A Low-Cost Force Feedback Joystick and Its use in PC Video Games," IEEE Transactions on Consumer Electronics, vol. 41, No. 3, Aug. 1995.

Ouhyoung et al., "The Development of A Low-Cost Force Feedback Joystick and Its Use in the Virtual Reality Environment," Proceedings of the Third Pacific Conference on Computer Graphics and Applications, Pacific Graphics '95, Seoul, Korea, Aug. 21-24, 1995.

Patrick et al., "Design and Testing of A Non-reactive, Fingertip, Tactile Display for Interaction with Remote Environments," Cooperative Intelligent Robotics in Space, Rui J. deFigueiredo et al., Editor, Proc. SPIE vol. 1387, pp. 215-222, 1990.

Pimentel et al., "Virtual Reality: through the new looking glass," $2^{nd}$ Edition; McGraw-Hill, ISBN 0-07-050167-X, pp. 41-202, 1994.

Rabinowitz et al., "Multidimensional tactile displays: Identification of vibratory intensity, frequency, and contactor area," Journal of The Acoustical Society of America, vol. 82, No. 4, Oct. 1987.

Russo, "The Design and Implementation of a Three Degree of Freedom Force Output Joystick," MIT Libraries Archives Aug. 14, 1990, pp. 1-131, May 1990.

Russo, "Controlling Dissipative Magnetic Particle Brakes in Force Reflective Devices," DSC-vol. 42, Advances in Robotics, pp. 63-70, ASME 1992.

Scannell, "Taking a Joystick Ride," Computer Currents, Boston Edition, vol. 9, No. 11, Nov. 1994.

Shimoga, "Finger Force and Touch Feedback Issues in Dexterous Telemanipulation," Proceedings of Fourth Annual Conference on Intelligent Robotic Systems for Space Expploration, Rensselaer Polytechnic Institute, Sep. 30-Oct. 1, 1992.

Snow et al., "Model-X Force-Reflecting-Hand-Controller," NT Control No. MPO-17851; JPL Case No. 5348, pp. 1-4, Jun. 15, 1989.

Stanley et al., "Computer Simulation of Interacting Dynamic Mechanical Systems Using Distributed Memory Parallel Processors," DSC-vol. 42, Advances in Robotics, pp. 55-61, ASME 1992.

Tadros, "Control System Design for a Three Degree of Freedom Virtual Environment Simulator Using Motor/Brake Pair Actuators", MIT Archive © Massachusetts Institute of Technology, pp. 1-88, Feb. 1990.

Terry et al., "Tactile Feedback in a Computer Mouse," Proceedings of Fouteenth Annual Northeast Bioengineering Conference, University of New Hampshire, Mar. 10-11, 1988.

* cited by examiner

PIVOTABLE COMPUTER INTERFACE

CROSS-REFERENCES TO RELATED APPLICATIONS

This application claims the benefit of U.S. Provisional Patent Application Ser. No. 60/305,958, filed Jul. 16, 2001, entitled "PIVOTABLE COMPUTER INTERFACE," the contents of which are hereby incorporated in its entirety for all purposes.

BACKGROUND OF THE INVENTION

The present invention relates to interfacing a user with a computer.

Users interface with electronic and mechanical devices in a variety of applications, and the need for a more natural, easy-to-use, and informative interface is a constant concern. In the context of the present invention, a user interfaces with computer devices for a variety of applications. One such application is interacting with computer-generated environments, such as virtual reality environments, including surgical simulations, games, actual surgeries and other application program generated environments. Computer input devices such as mice and trackballs are often used to control a cursor within a graphical environment and provide input in these applications.

In some interface devices, force feedback and/or tactile feedback is also provided to the user, collectively known herein as "haptic feedback." For example, haptic versions of joysticks, mice, gamepads, steering wheels, or other types of devices may output forces to the user based on events or interactions occurring within the graphical environment, such as in a game or other application program. In a computer simulation, it is often desirable to graphically represent a user or a portion of the user in the graphical environment and to allow the user to realistically interact with the graphical environment.

SUMMARY OF THE INVENTION

The present invention provides a computer interface for use with a computer simulation system. The interface includes a first grip portion and a second grip portion pivotably coupled to the first grip portion. An actuator is coupled to at least one of the two grip portions and is configured to provide feedback to a user.

In accordance with one aspect of the present invention, the actuator is coupled to both the first and second grip portions.

In accordance with another aspect of the present invention, the actuator comprises a rotary motor.

In accordance with a further aspect of the present invention, the actuator is coupled to the first grip portion and comprises a rotary motor, a rotating shaft that extends into the second grip portion and a cable coupled to the rotating shaft and the second grip portion.

In accordance with another aspect of the present invention, the computer interface further includes a spring coupled to both the first and second grip portions.

In accordance with a further aspect of the present invention, the computer interface includes at least one sensor for sensing angular rotation of a pivot coupling the first and second grip portions.

In accordance with yet a further aspect of the present invention, the feedback is at least one of a group comprising pushing the grip portions apart, pulling the grip portions together, vibration, torque and noise.

In accordance with another aspect of the present invention, the interface comprises a practice tool comprising an elongated portion and a handle. The handle includes the first and second grip portions and the actuator is coupled to at least one of the two grip portions.

In accordance with another aspect of the present invention, a sensor is provided that senses at least one of motion and position of the elongated portion.

In accordance with another aspect of the present invention, a method of providing feedback within a practice tool during computerized simulation includes providing a practice tool comprising an elongated portion and a handle, the handle comprises a first grip portion at a proximal portion of the elongated portion, a second grip portion at a proximal portion of the elongated portion and pivotably coupled to the first grip portion, and an actuator coupled to at least one of the first and second grip portions. Feedback is provided with the actuator to a user.

Other features and advantages of the present invention will be understood upon reading and understanding the description of the preferred exemplary embodiments, found hereinbelow, in conjunction with reference to the drawings, in which like numerals represent like elements.

DESCRIPTION OF EXEMPLARY EMBODIMENTS OF THE INVENTION

The present invention relates to computer simulations and more particularly to computer simulations involving the control of a graphical image, such as a graphical image that is a graphical representation of an instrument being manipulated by a user. Although the process is illustrated at least partly in the context of a surgical simulation interface, the present invention may be used in other simulation and computer interactive processes and/or to control other graphical images and should not be limited to the examples provided herein.

Figure 1:
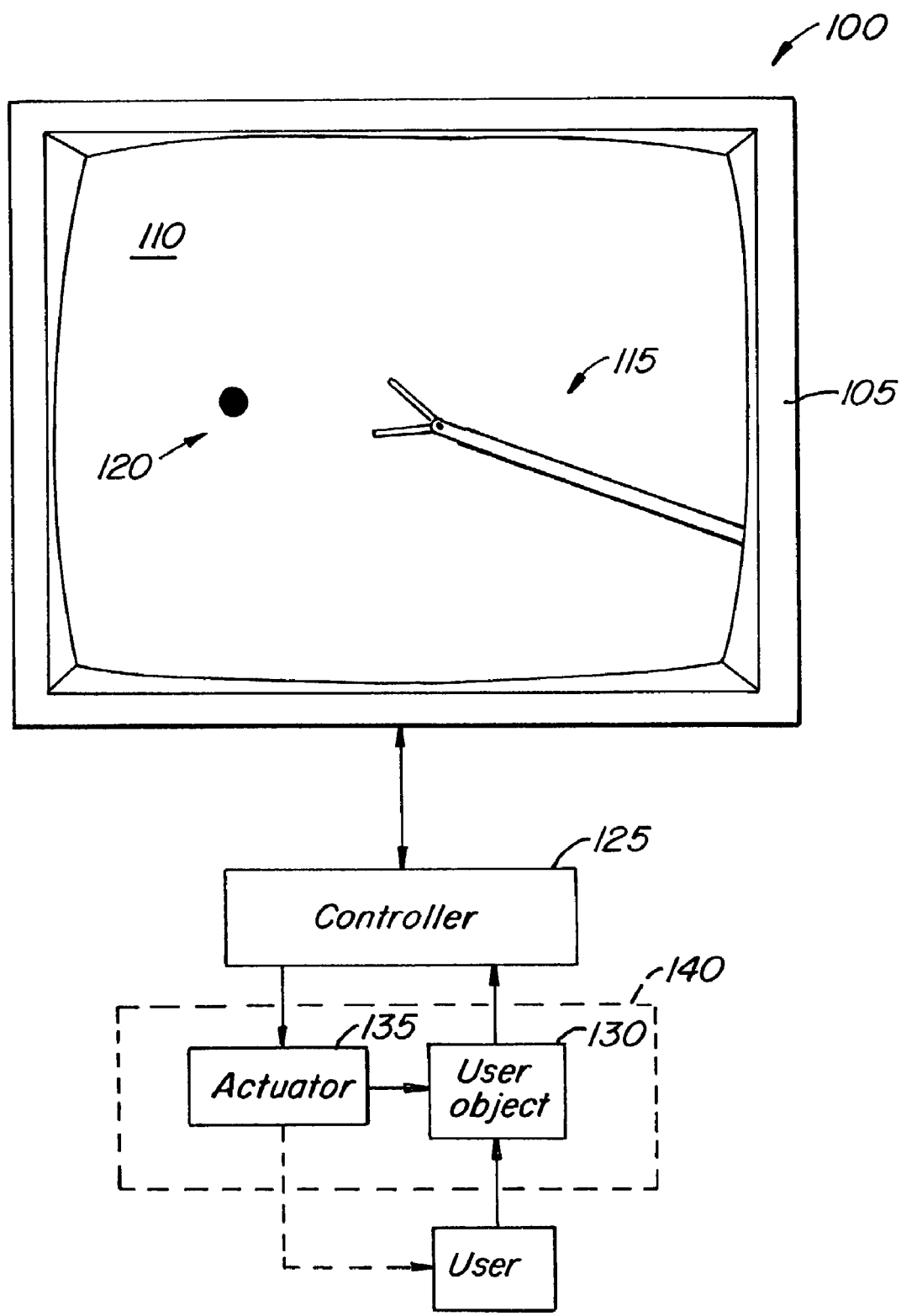
FIG. 1 is a schematic diagram of a computer interface system according to the present invention.

FIG. 1 is a schematic illustration of a computer interface system 100 according to the invention. The computer interface system 100 is capable of generating a computer generated or virtual reality environment. A display 105 provides a graphical environment 110 to a user. Within the graphical environment 110 is a graphical image 115. The graphical image 115 may be, for example, a cursor or other graphical object, the position, movement, and/or shape of which is controllable. For example, the graphical image 115 may be a pointer cursor, a character in a game, a surgical instrument, a view from the end of a surgical instrument, a representative portion of the user, or the like. Also within the graphical environment is a graphical object 120 such as a round object, as shown, or any other graphical representation including another graphical image that may be controlled by the user or by another user. A controller 125 in communication with the display 105 is capable of generating and/or controlling the graphical environment 110, for example by executing program code including an application program related to a simulation. A user object 130 is manipulatable by a user, and the manipulation of the user object 130 controls the position, orientation, shape and/or other characteristic of the graphical image 115 within the graphical environment 110, for example by directly correlating a position of the user object 130 with a displayed position and/or shape of the graphical image 115 or by correlating a position of the user object 130 with a rate of movement and/or change of shape of the graphical image 115. Either the entire user object 130 may be manipulatable by the user or a portion of the user object 130 may be manipulatable relative to another portion of the user object 130. For example, the user object may be a surface that is engaged by one or more hands of a user, such as a joystick, a mouse, a mouse housing, a stylus, a knob, an elongated rigid or flexible member, an instrumented glove, or the like and may be moveable in from one to six degrees of freedom.

Optionally, haptic feedback may be provided to the user to increase the realism of the virtual reality environment. For example, when a predetermined event occurs within the graphical environment 110, such as an interaction of the graphical image 115 with the graphical object 120, the controller 125 may cause an actuator 135 to output a haptic sensation to the user. In the version shown, the actuator 135 outputs the haptic sensation to the user object 130 through which the sensation is provided to the user. The actuator 135 and the user object 130 may be part of a haptic interface device 140. The actuator 135 may be positioned in the haptic interface device 140 to apply a force to the user object 130 or to a portion of the user object.

The actuator 135 may provide the haptic sensation actively or passively. For example, the actuator 135 may comprise one or more motors coupled to the user object 130 to apply a force to the user or to the user object 130 in one or more degrees of freedom. Alternatively or additionally, the actuator 135 may comprise one or more braking mechanisms coupled to the user object to inhibit movement of the user or the user object 130 in one or more degrees of freedom. By haptic sensation it is meant any sensation provided to the user that is related to the user's sense of touch. For example, the haptic sensation may comprise kinesthetic force feedback and/or tactile feedback. By kinesthetic force feedback it is meant any active or passive force applied to the user to simulate a force that would be experienced in the graphical environment 110, such as a grounded force applied to the user or the user object 130 to simulate a force experienced by at least a portion of the graphical image 115. For example, if the graphical image 115 is positioned against a surface, a barrier or an obstruction, the actuator 135 may output a force against the user object 130 preventing or retarding movement of the user or the user object 130 in the direction of the barrier or obstruction. By tactile feedback it is meant any active or passive force applied to the user to provide the user with a tactile indication of a predetermined occurrence within the graphical environment 110. For example, a vibration, click, pop, or the like may be output to the user when the graphical image 115 interacts with a graphical object 120. Additionally, tactile feedback may comprise a tactile sensation applied to approximate or give the illusion of a kinesthetic force. For example, by varying the frequency and/or the amplitude of an applied vibration, variations in surface textures of different graphical objects may be simulated or by providing a series of clicks when a graphical image penetrates an object, resistance to the penetration may be simulated. For example, in one version a kinesthetic force sensation, such as a spring force, may be applied to the user whenever the graphical image 115 engages the graphical object 120 to simulate a selectively deformable surface. Alternatively or additionally, a tactile sensation, such as a pop, may be applied to the user when the graphical image 115 is moved across a surface of the graphical object 120 to simulate a texture of the graphical object 120.

Figure 2:
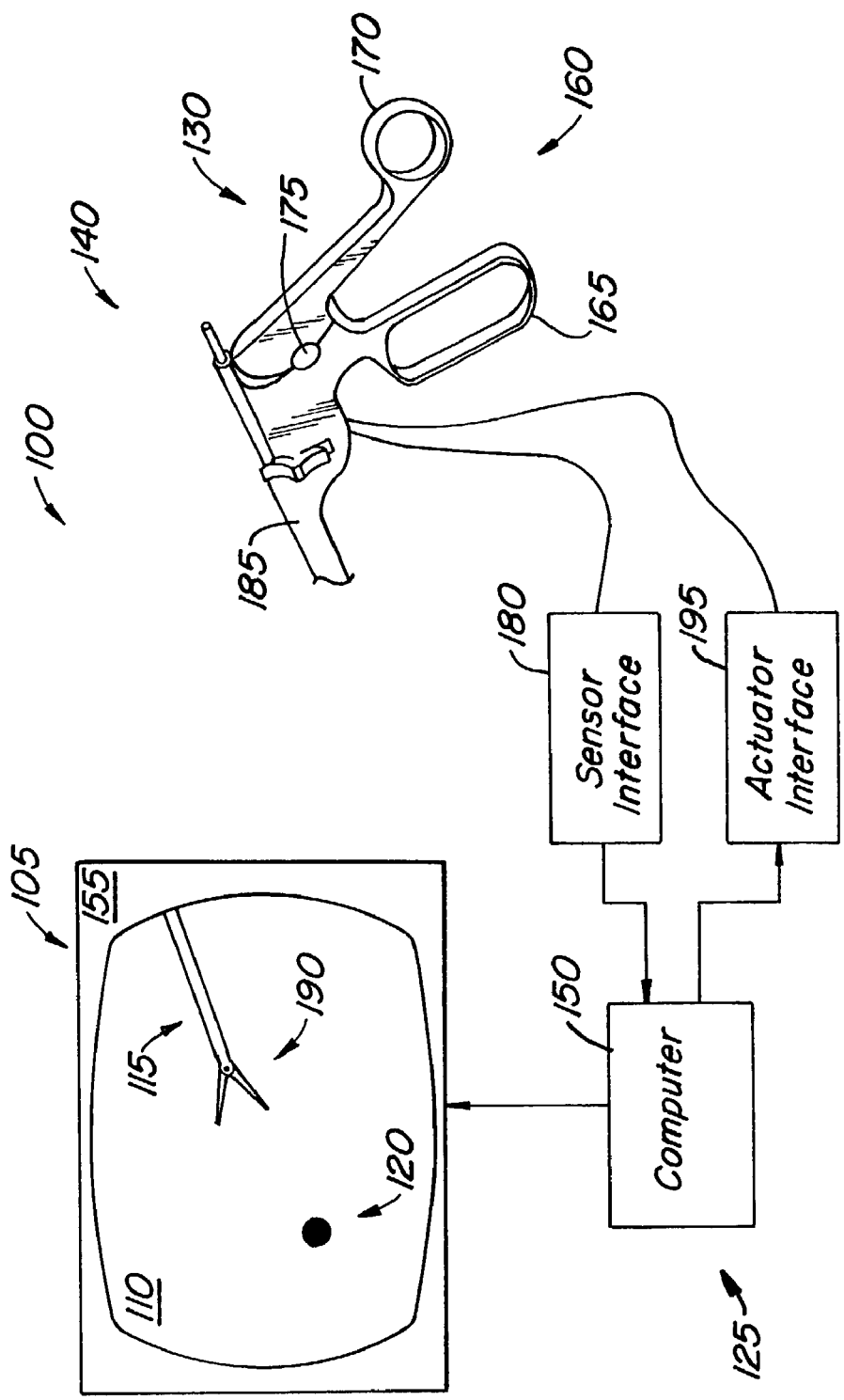
FIG. 2 is a schematic diagram of a computer interface system according to the present invention comprising an instrument with a pivoting handle.

The controller 125 may be a computer 150, or the like, such as the computer shown in FIG. 2. In one version, the computer 150 may comprise a processor and may be able to execute program code. For example, the computer may be a personal computer or workstation, such as a PC compatible computer or Macintosh personal computer, or a Sun or Silicon Graphics workstation. The computer 150 may be operable under the Windows™, MacOS, Unix, or MS-DOS operating system or similar. Alternatively, the computer 150 may be one of a variety of home video game console systems commonly connected to a television set or other display, such as systems available from Nintendo, Sega, or Sony. In other embodiments, the computer 150 may be a "set top box" which may be used, for example, to provide interactive television functions to users, or a "network-" or "internet-computer" which allows users to interact with a local or global network using standard connections and protocols such as used for the Internet and World Wide Web. The computer 150 may include a host microprocessor, random access memory (RAM), read only memory (ROM), input/output (I/O) circuitry, and/or other components of computers well-known to those skilled in the art. The computer 150 may implement an application program with which a user is interacting via peripherals, such as haptic interface device 140 and/or user object 130. For example, the application program may be a simulation program, such as a medical procedure simulation program, a game, a computer aided design or other graphic design program, an operating system, a word processor or spreadsheet, a Web page or browser that implements, for example, HTML or VRML instructions, a scientific analysis program, or other application program that may or may not utilize haptic feedback. Herein, for simplicity, operating systems such as Windows™, MS-DOS, MacOS, Linux, Be, etc. are also referred to as "application programs." The application program may comprise an interactive graphical environment, such as a graphical user interface (GUI) to allow the user to input information to the program. Typically, the application provides images to be displayed on a display screen 155 and/or outputs other feedback, such as auditory signals. The computer 150 is capable of generating a graphical environment 110, which may be a graphical user interface, game, simulation, such as those described above, or other visual environment. The computer 150 displays graphical objects 120, such as graphical representations and graphical images, or "computer objects," which are not physical objects, but are logical software unit collections of data and/or procedures that may be displayed as images by the computer on display screen 155, as is well known to those skilled in the art. The application program checks for input signals received from the electronics and sensors of the user object 130, and outputs force values and/or commands to be converted into haptic output for the actuator 135. Suitable software drivers which interface such simulation software with computer input/output (I/O) devices are available from Immersion Corporation of San Jose, Calif. Display screen 155 may be included in the computer and may be a standard display screen (LCD, CRT, flat panel, etc.), 3-D goggles, or any other visual output device.

In one version of the computer interface system 100, the user object 130 comprises a handle of at least a portion of a real or mock instrument 160, such as a surgical instrument used in laparoscopic surgery. In the version shown in FIG. 2, the instrument 160 comprises a handle having a first grip 165 and a second grip 170. The first grip 165 and the second grip 170 are relatively pivotable about a pivot 175. Manipulation of the handle may be detected by one or more sensors in, on, or in communication with the user object 130. A signal indicative of the detected manipulation is provided to the computer 150, optionally through sensor interface 180, to control the position, orientation, and/or shape of the graphical image 115. For example, the sensors may detect the motion or position of an elongated portion 185 of the instrument 160 in from one to six or more degrees of freedom to control the displayed position of the graphical image 115, as disclosed in U.S. Pat. Nos. 5,623,582; 5,821,920; 5,731,804; and 5,828,197 each of which is incorporated herein by reference in its entirety. Alternatively or additionally, one or more sensors may be positioned to detect manipulation of the first grip 165 relative to the second grip 170, for example by sensing the amount of rotation about pivot 175. The sensed pivoting may then be used to control the shape of the displayed graphical image 115. For example, in the version shown, pivoting the first grip 165 relative to the second grip 170 may result in an opening or closing of jaws 190 on the distal end of the graphical image 115. In this way, a user may be able to manipulate the instrument 160 to cause the graphical image 115 to grasp or otherwise engage the graphical object 120.

In use, a user contacts the instrument 160 to interact with the graphical environment 110. In the version shown in FIG. 2, the user grasps the handle including the first grip 165 and the second grip 170 and manipulates the instrument 160 by causing rotation of the grips and optionally by manipulating the instrument 160 in additional degrees of freedom. For example, the user may cause the instrument 160 to move to his or her left and downwardly to cause the graphical image 115 to be rendered so as to appear to touch the graphical object 120. In addition, the user may rotate the grips to make the graphical jaws 190 appear to grasp the graphical object 120.

The realism of the graphical environment interaction may be increased by providing an actuator 135 adapted to provide one or more haptic sensations to the user during the user's interaction with the graphical environment 110. The actuator may either provide the haptic sensation directly to the user or may apply the haptic sensation to the user through the user object, for example by applying a force to the user through the instrument 160. This allows the user to not only visualize the graphical image 115 contacting the graphical object 120, but also to receive an indication through the user's sense of touch that the object has been contacted, thereby providing a more immersive experience. In one version, the actuator 135 may be positioned to provide a haptic sensation to the first grip 165 and/or to the second grip 170 to simulate gripping forces associated with the relative rotation of the grips. It has been discovered that by providing a haptic sensation to the user simulating the griping forces, the user's perception of realistic interaction with a graphical object 120 is enhanced. For example, a haptic sensation may be provided to the grips in coordination with the graphical jaws 190 grasping the graphical object 120 to simulate an actual grasping of an object.

Accordingly, in the version of FIG. 2, the computer 150 controls the output of a haptic sensation to the instrument 160 by providing a signal, optionally though actuator interface 195, to cause the palm forcing mechanism to be actuated.

Figure 3:
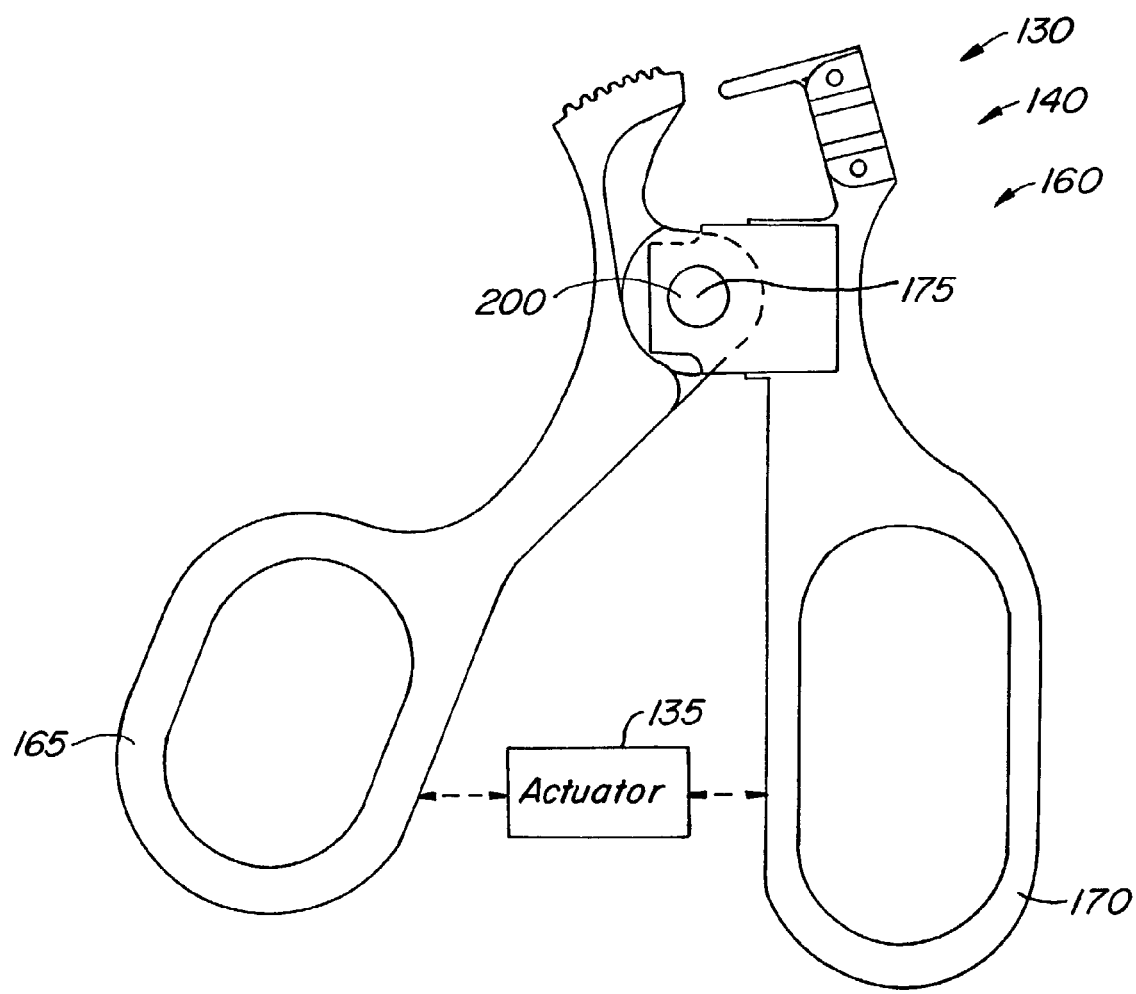
FIG. 3 is a schematic diagram of an embodiment of a haptic interface device according to the present invention.

A version of a haptic interface 140 is shown in FIG. 3. One or more angle sensors 200 may be positioned to detect the angular rotation about the pivot 175. In a relatively simple version, a single digital or analog sensor detects either an open condition or a closed condition of the grips, and the computer 150 correspondingly displays the graphical jaws 190 either as being open or as being closed or grasping an object in the graphical environment 110. In another version, the angle sensor 200 may comprise a sensor that provides a variable signal by which the display of the graphical jaws 190 may be controlled. The joint angle sensor may comprise one or more of an optical, electrical, or magnetic encoder, a stain gage, a fiber optic sensor, a potentiometer, or the like. The actuator 135 may be positioned to force apart and/or to bring together the first grip 165 and the second grip 170.

Figure 4:
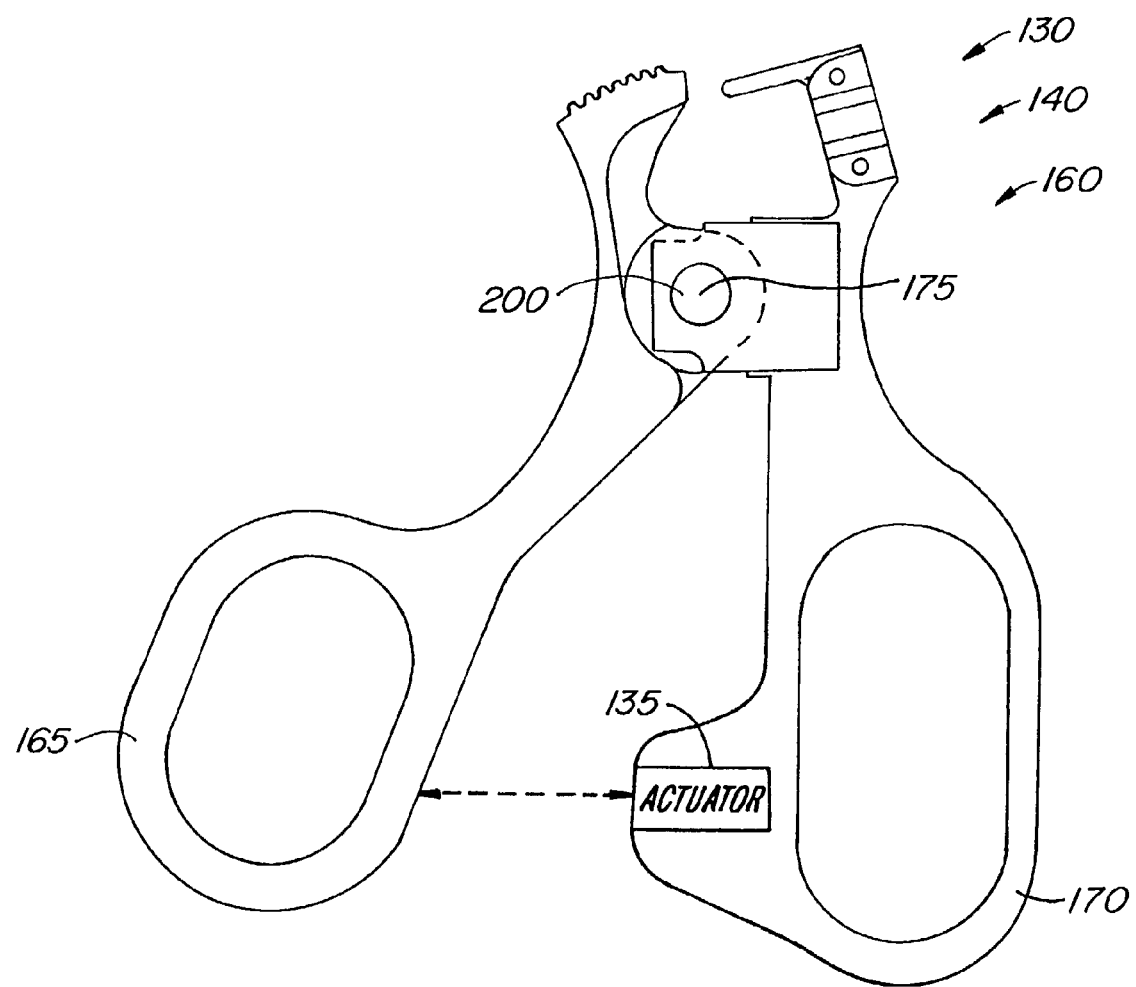
FIG. 4 is a schematic diagram of another embodiment of a haptic interface device according to the present invention.

An ungrounded version of a haptic interface 140 is shown in FIG. 4. In this version, the actuator 135 is housed in or on the second grip 170. The actuator is capable of actuating the first grip 165 toward or away from the second grip 170. With this version, the instrument 160 need not be grounded in order to provide haptic sensations related to rotation of the grips.

Figure 5:
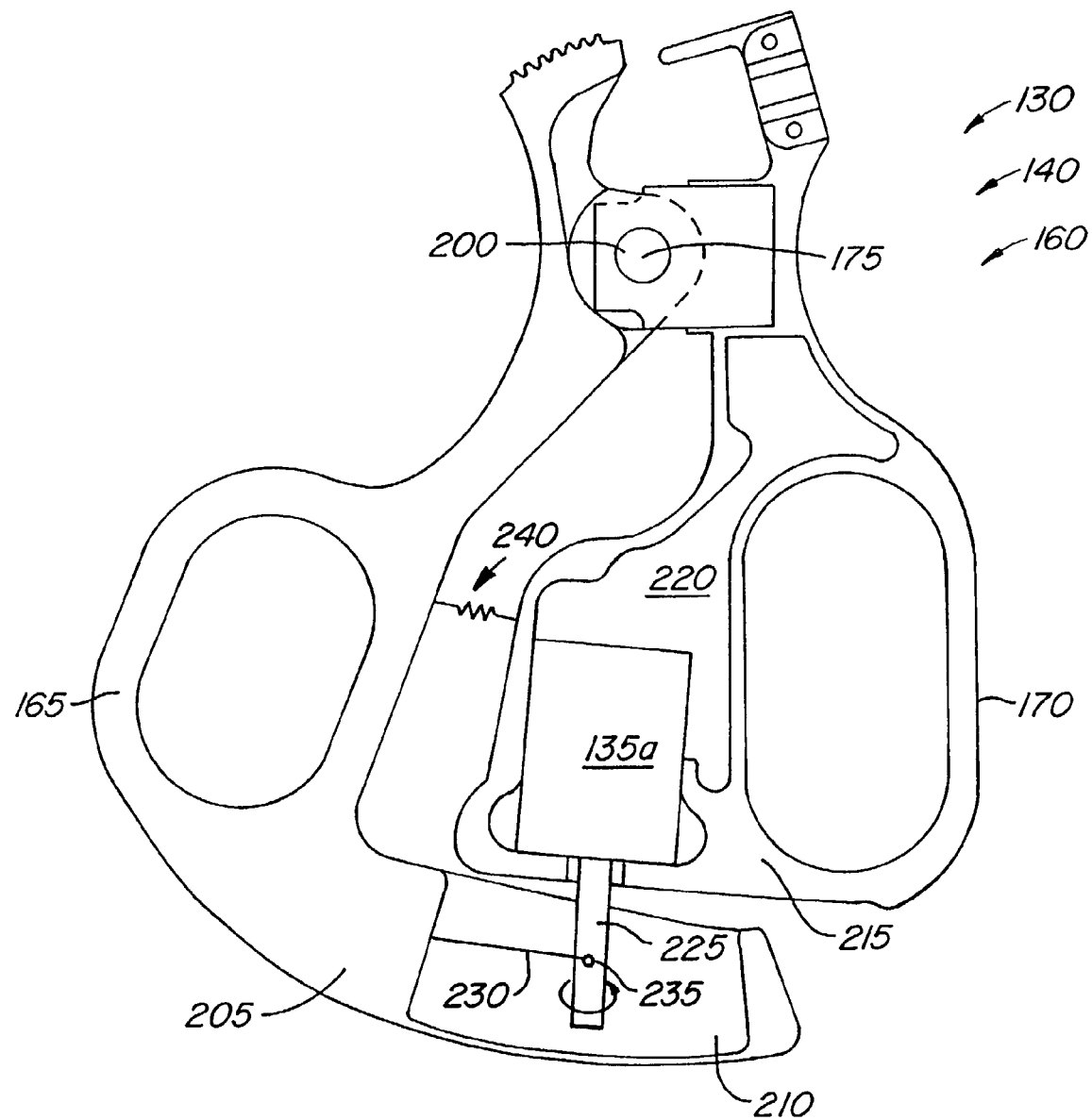
FIG. 5 is a schematic diagram of another embodiment of a haptic interface device according to the present invention.

The actuator 135 may comprise a rotary motor 135a, as shown for example in the version of FIG. 5. In this version, the first grip 165 comprises an extension 205 and the second grip 170 comprises an extension 215. The extensions 205, 215 overlap one another as shown in FIG. 5. The extension 215 of the second grip 170 includes a recessed portion 220 which receives the rotary motor actuator 135a and which grounds the motor 135a to the second grip 170. The motor 135a is capable of rotating a shaft 225 extending therefrom. The shaft 225 extends into a recessed portion 210 in the first grip extension 205. A cable 230 is fixed to the first grip 165, for example, by being fixed to the wall of the recessed portion 210 of the extension 205. The other end of the cable 230 is fixed to the rotatable shaft 225, for example by being fixed within a through bore 235 in the shaft 225. Rotation of the shaft 225 in the direction of the arrow causes the cable 230 to wrap around the shaft 225 and pulls the first grip 165 toward the second grip 170. Accordingly, actuation of the motor 135a may cause a grasping force to be applied to the instrument 160. This grasping force may be a haptic sensation related to interactions in the graphical environment. Additionally or alternatively, the grasping force may be used to augment, amplify or reduce the force the user is applying to the interface device 165. Optionally, a spring 240 which biases the grips toward an open position may be used to counteract the grasping force generated by the actuator 135a.

Figure 6:
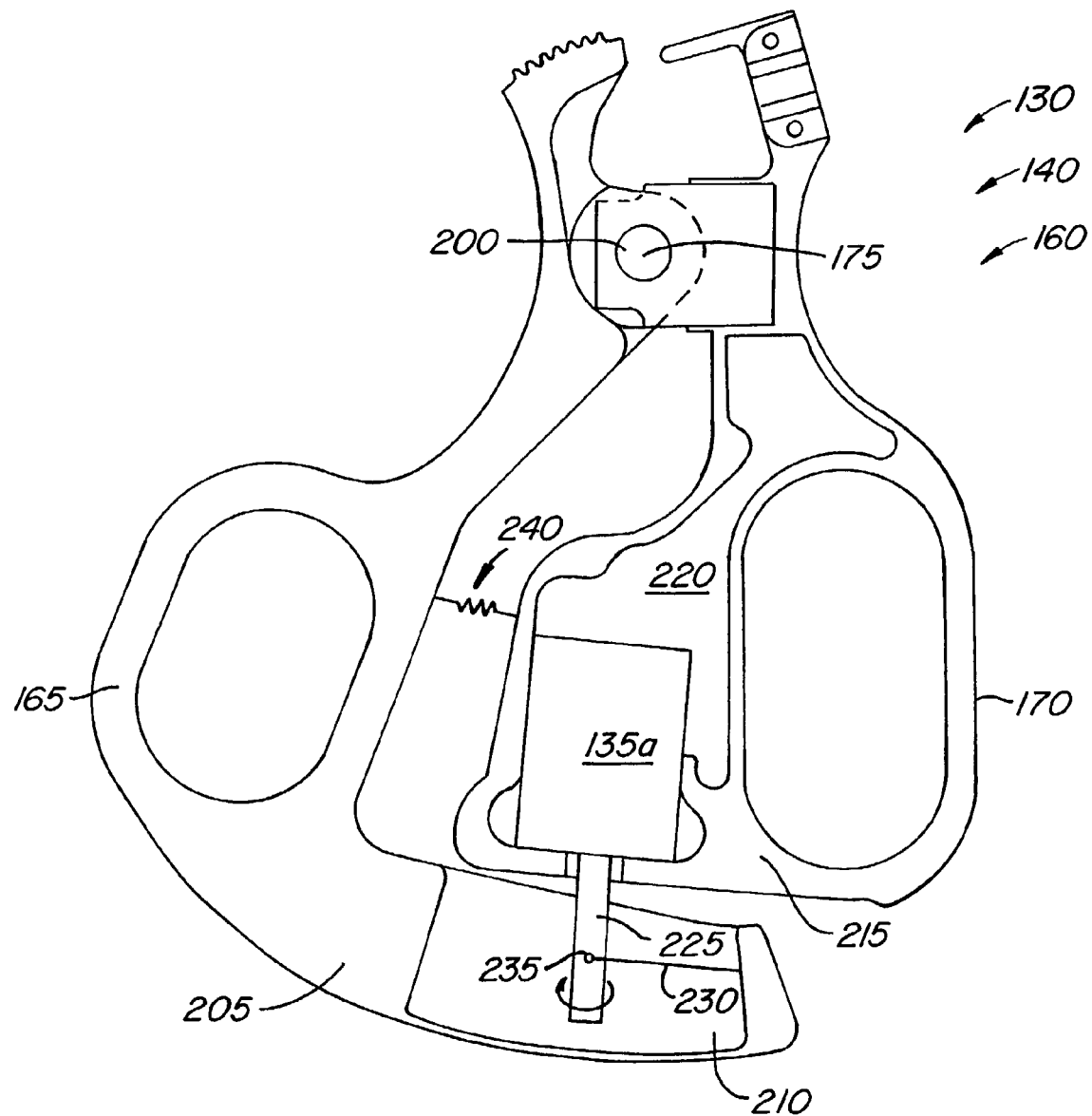
FIG. 6 is a schematic diagram of another embodiment of a haptic interface device according to the present invention.

Alternatively, the rotary motor actuator 135a may be used to generate a force opposing the closing of the grips, as shown in FIG. 6. In the version of FIG. 6, the cable 230 is fixed to the opposite side of the recess 210 in the extension 205 of the first grip 165. Thus, as the shaft 225 is rotated in the direction of the arrow in FIG. 6, the first grip 165 and the second grip 170 are forced apart. This generated force may also be used for haptic sensations. For example, when the graphical jaws 190 contact the graphical object 120 a force may be output to the user preventing or inhibiting the closing of the grips in relation to the displayed activity. Alternatively or additionally, the applied force may be used to augment, amplify or reduce the force applied by the user, as discussed above. In the version of the FIG. 6, the spring 240 is optionally provided to bias the grips towards one another.

Figure 7:
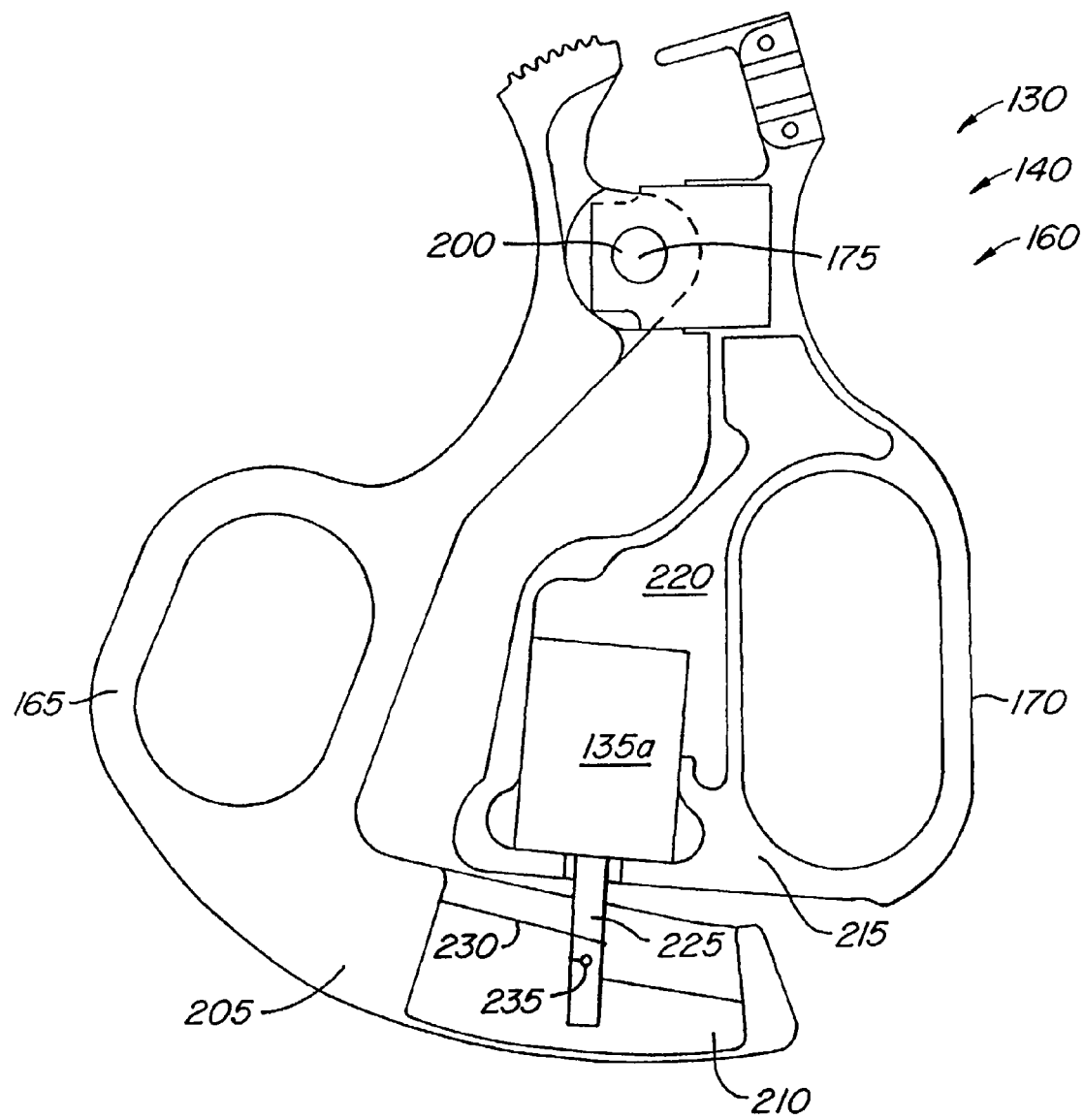
FIG. 7 is a schematic diagram of another embodiment of a haptic interface device according to the present invention.

Another version of the haptic interface 140 is shown in FIG. 7. In this version, the rotary motor actuator 135*a* and rotatable shaft 225 are able to actively applied either a closing or an opening force to the grips. In the version of FIG. 7, the rotatable shaft 225 is used as a capstan-type device. One end of the cable 230 is fixed to one side of the recess 210 and the other end of the cable 230 is fixed to the other side of the recess 210. The cable is wrapped around the rotatable shaft 225 and extends through the throughbore 235. Thus, rotation of the rotatable shaft 225 in one direction causes an opening force to be applied to the grips and rotation in the other direction causes a closing force to be applied to the grips.

Figure 8:
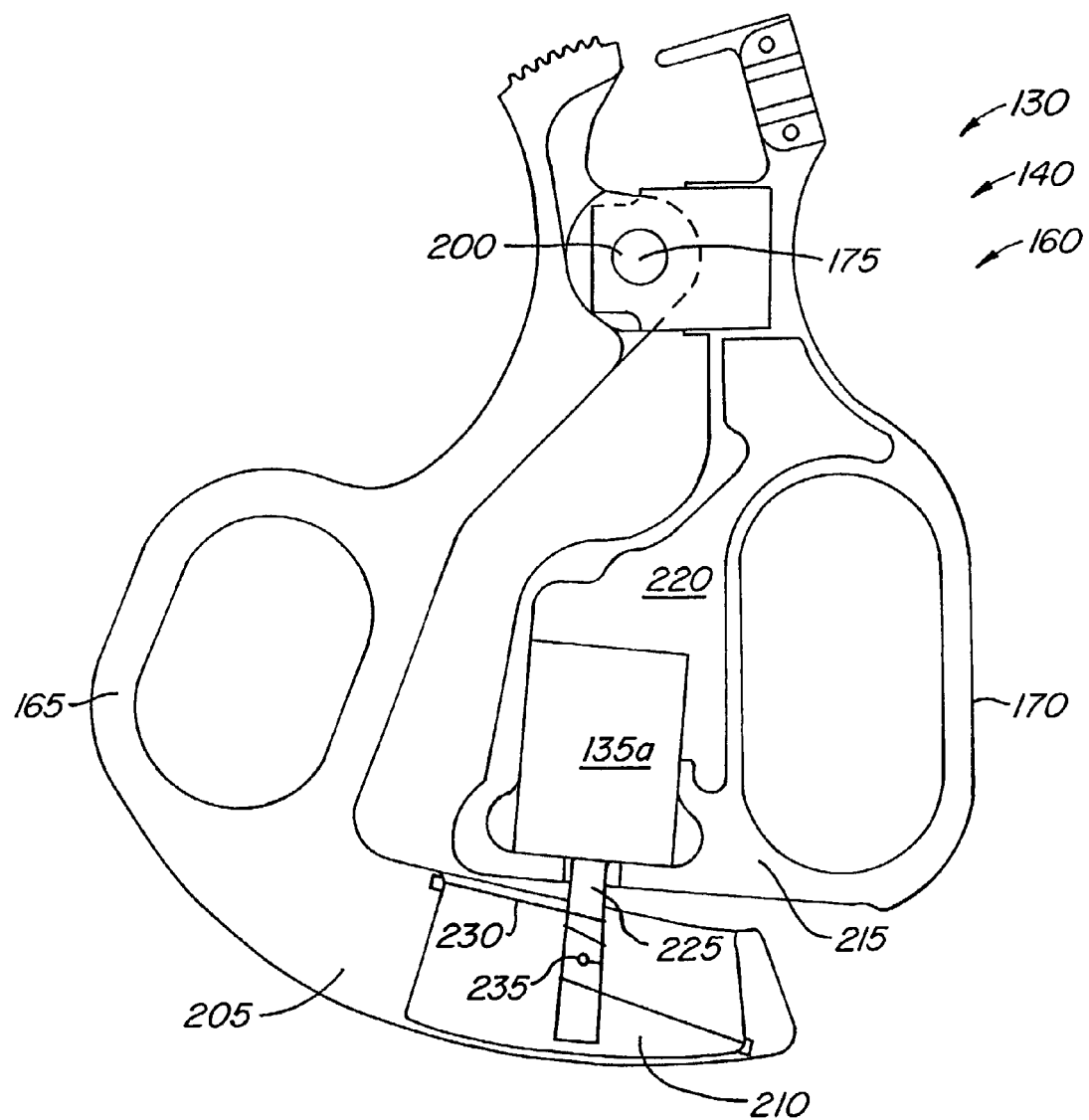
FIG. 8 is a schematic diagram of another embodiment of a haptic interface device according to the present invention.

FIG. 8 shows a version similar to the version of FIG. 7 but with a tapered rotatable shaft 225. The tapered rotatable shaft 225 allows for a greater range of motion between the grips. The taper allows the uptake of the amount of cable on the shaft to be substantially the same as the amount of cable discharged from the shaft throughout the range of travel of the shaft within the recess 210. In this way, the amount of slack in the cable is reduced which reduces backlash and which maintains tight contact of the cable on the shaft. In one version, the tapered shaft 225 is conically shaped. In a particularly useful version, the sides of the conically shaped shaft 225 are shaped such that an extension thereof would result in the sides intersecting substantially at the pivot 175. In another version, the shaft may be stepped.

Figure 9:
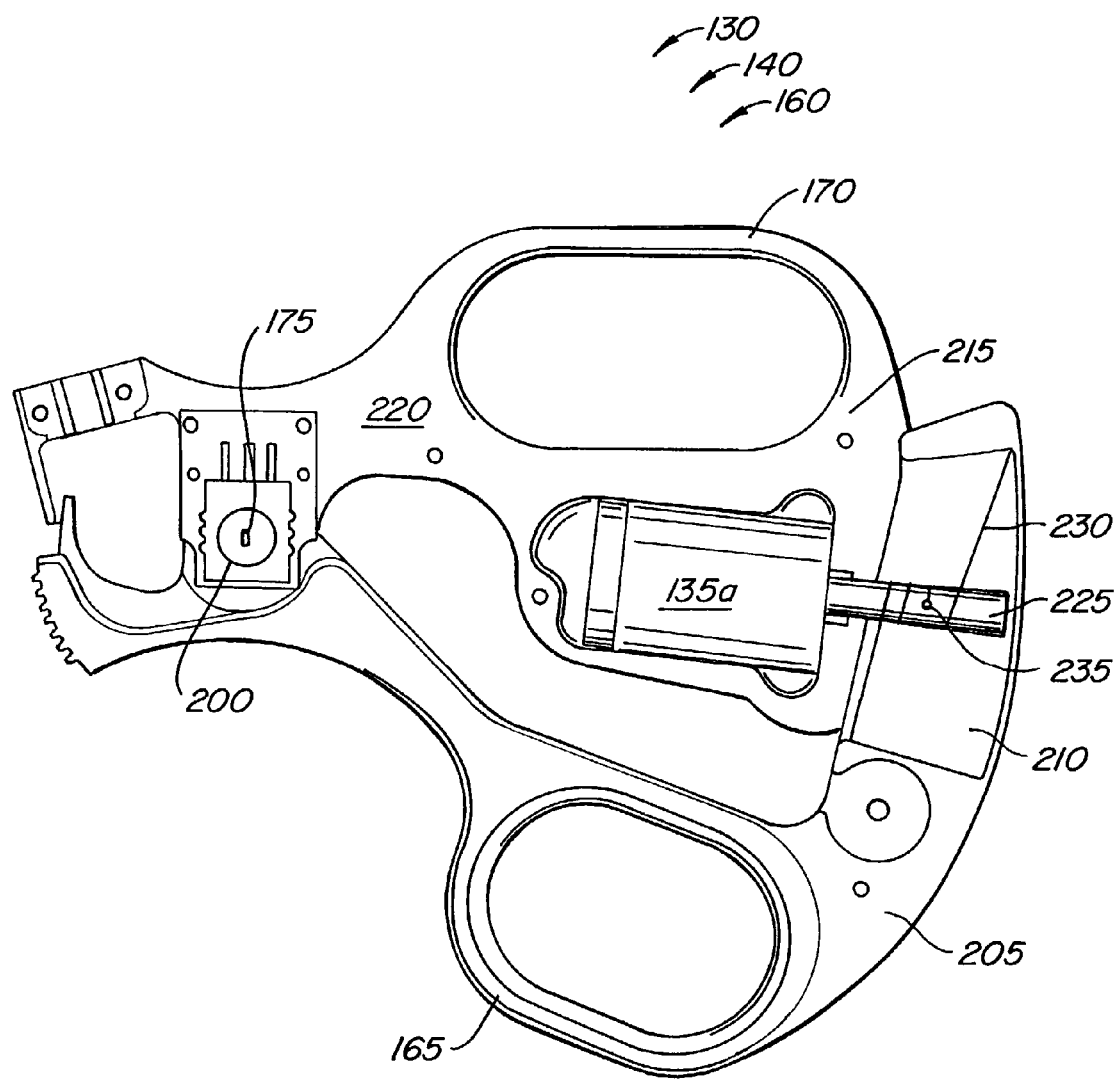
FIGS. 9-11 are additional views of the haptic interface device of FIG. 8.
Figure 10:
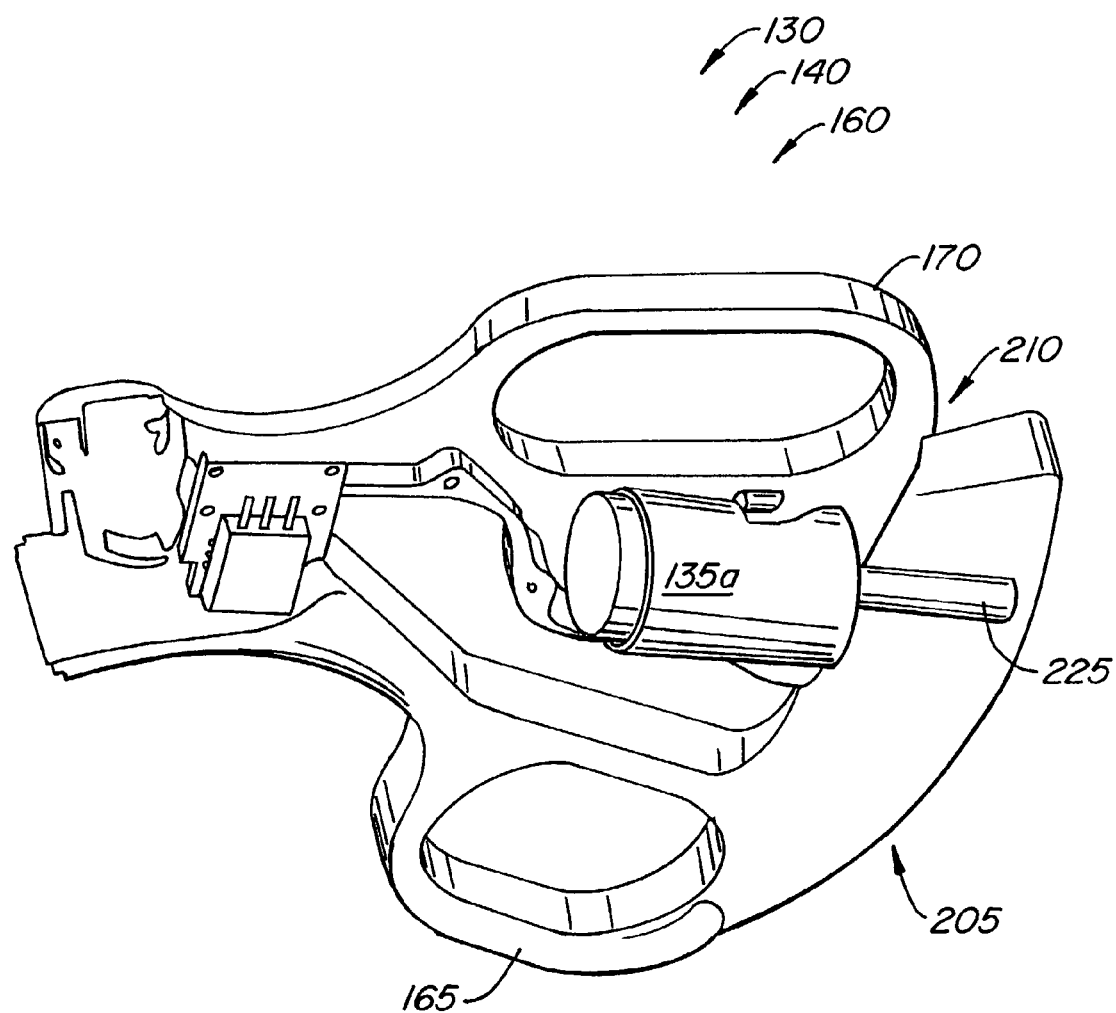
Figure 11:
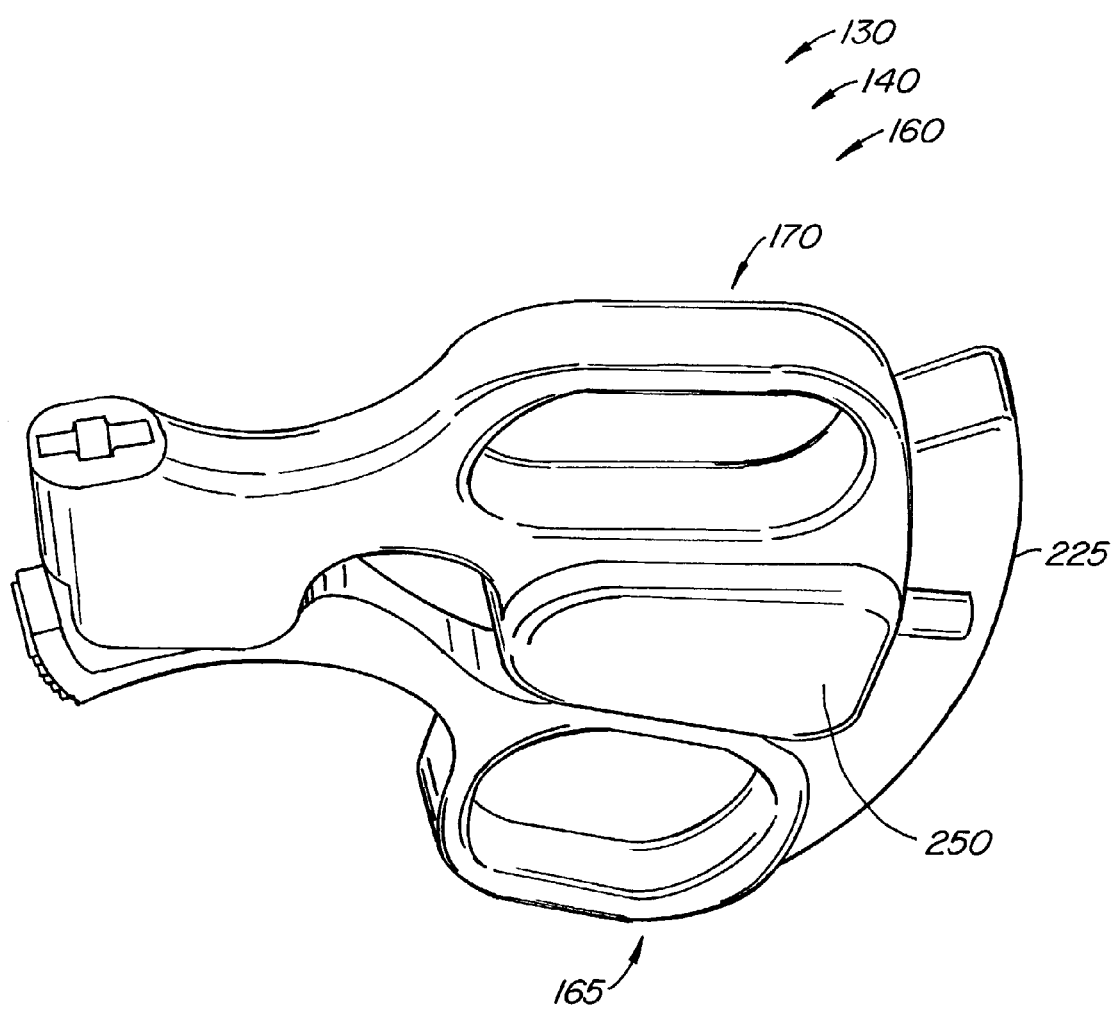

FIGS. 9 and 10 show top and side perspective views of the haptic interface device 140 of FIG. 8. FIG. 11 shows the haptic interface device 140 of FIG. 8 with a cover 250 covering the motor 135*a*.

Figure 12:
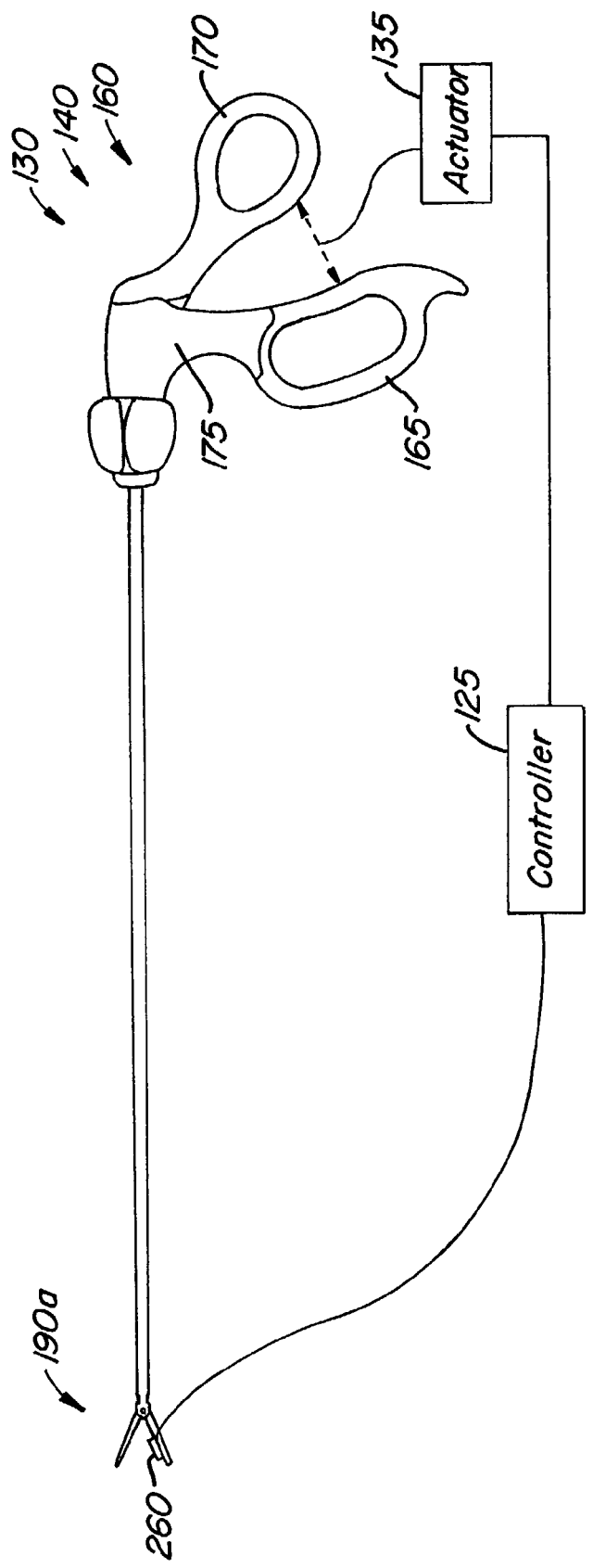
FIG. 12 is a schematic side view of an instrument with a sensor and an actuator.

FIG. 12 shows a version of in which an actual surgical instrument is the interface device 140. The surgical instrument, which is a laparoscopic instrument in the version shown, may include a distal end that is controllable by manipulation of the handle. For example, the distal end may comprise jaws 190*a* that may be opened and closed by opening and closing the grips 165,170 of the handle. The surgical instrument handle may also comprise an actuator 135, such as one of the actuating mechanisms discussed above, for forcing the grips open or closed. The actuator 135 may be used to assist the user in applying forces or may be used to reduce the force a user applies to the grips or may be used to apply a haptic sensation to the user. In one version, a sensor 260 may be provided to detect a condition at the distal end of the surgical instrument. For example, a pressure or force sensor may be positioned to detect the pressure or forces applied to one or more of the jaws 190*ab*. The sensed condition may be provided to the controller which may be a separate controller or may be a controller or logic on the surgical instrument. The controller may then control the operation of the actuator 135 in relation to the sensed condition. For example, often the mechanical linkage is insufficient to communicate to the user that the jaws have interacted with an object. Thus, the sensor may be sufficiently sensitive to detect a predetermined interaction, and the controller may cause a haptic response to be applied to the user to indicate the interaction. Additional interactions are discussed in U.S. patent application Ser. No. 09/811,358 filed on Mar. 16, 2001 which is incorporated herein by reference in its entirety.

While this invention has been described in terms of several preferred embodiments, it is contemplated that alterations, permutations and equivalents thereof will become apparent to those skilled in the art upon a reading of the specification and study of the drawings. For example, when used with a simulation system, laparoscopic techniques other than those discussed above may be simulated. For example, other techniques are disclosed in the following U.S. patents, all of which are incorporated herein by reference in their entireties: U.S. Pat. Nos. 5,735,874; 5,514,156; 5,163,945; 5,980,510; 5,632,432; 6,168,605; 5,258,004; 5,307,976; 5,447,513; 5,681,324; 6,090,120; and 5,846,254. Additionally, the simulation may comprise surgical applications other than laparoscopic procedures. Furthermore, the interface device may be used for non-surgical simulations. For example, an application program may be responsive to a shear interface and may comprise instructional program code on how to correctly prune a rose bush or a game environment may use pivotal grip haptic feedback. Additionally, the forcing mechanisms disclosed may be used to apply forces to relatively pivoting parts in any environment.

What is claimed is:

1. A computer interface for use with a computer simulation system, the computer interface comprising:
   a first grip portion of the computer interface;
   a second grip portion of the computer interface pivotably coupled to the first grip portion at a pivot point; and
   an actuator mechanically coupled to the first or second grip portions and configured to provide haptic feedback to a user, wherein the haptic feedback comprises a force about the pivot point applied to one of the first or second grip portions.

2. The computer interface of claim 1, wherein the actuator is coupled to both the first and second grip portions.

3. The computer interface of claim 2, wherein the actuator comprises a rotary motor.

4. The computer interface of claim 1, wherein the actuator is coupled to the first grip portion and comprises a rotary motor, a rotating shaft that extends into the second grip portion, and a cable coupled to the rotating shaft and the second grip portion.

5. The computer interface of claim 1, further comprising a spring coupled to both the first and second grip portions.

6. The computer interface of claim 1, further comprising at least one sensor for sensing angular rotation of the first and second grip portions about the pivot point.

7. The computer interface of claim 1, wherein the haptic feedback comprises at least one of kinesthetic feedback or vibrotactile feedback.

8. A computer interface for use with a computer simulation system, the computer interface comprising a practice tool comprising an elongated portion and a handle, the handle comprising:
   a first grip portion of the computer interface at a proximal portion of the elongated portion;
   a second grip portion of the computer interface at a proximal portion of the elongated portion and pivotably coupled to the first grip portion at a pivot point; and
   an actuator coupled to the first or second grip portions, the actuator configured to provide haptic feedback to a user, wherein the haptic feedback comprises a force about the pivot point applied to one of the first or second grip portions.

9. The computer interface of claim 8, wherein the actuator is coupled to both the first and second grip portions.

10. The computer interface of claim 9, wherein the actuator comprises a rotary motor.

11. The computer interface of claim 8, wherein the actuator is coupled to the first grip portion and comprises a rotary motor, a rotating shaft that extends into the second grip portion, and a cable coupled to the rotating shaft and the second grip portion.

12. The computer interface of claim 8, further comprising a spring coupled to both the first and second grip portions.

13. The computer interface of claim 8, further comprising at least one sensor for sensing angular rotation of the first and second grip portions about the pivot point.

14. The computer interface of claim 8, wherein the haptic feedback comprises at least one of kinesthetic feedback or vibrotactile feedback.

15. The computer interface of claim 8, further comprising at least one sensor for sensing at least one of motion or position of the elongated portion.

16. A method of providing haptic feedback to a practice tool during computerized simulation, the method comprising:
   providing a practice tool comprising an elongated portion and a handle, the handle comprising:
      a first grip portion of the practice tool at a proximal portion of the elongated portion;
      a second grip portion of the practice tool at a proximal portion of the elongated portion and pivotably coupled to the first grip portion at a pivot point; and
      an actuator coupled to the first or second grip portions; and
   providing haptic feedback with the actuator, wherein the haptic feedback comprises a force about the pivot point applied to one of the first or second grip portions.

17. The method of claim 16, wherein the haptic feedback comprises at least one of kinesthetic feedback or vibrotactile feedback.

18. The method of claim 16, further comprising sensing angular rotation of the first and second grip portions about the pivot point.

19. The method of claim 16, further comprising sensing at least one of motion or position of the elongated portion.

20. The method of claim 16, further comprising providing a spring coupled to the first and second grip portions.

* * * * *